United States Patent
Leben (10) Patent No.: US 8,097,861 B2
(45) Date of Patent: Jan. 17, 2012

(54) SYSTEM AND METHOD FOR GERMICIDAL SANITIZING OF AN ELEVATOR OR OTHER ENCLOSED STRUCTURE

(75) Inventor: David Leben, Wichita, KS (US)

(73) Assignee: Sound Health Designs, LLC, Wichita, KS (US)

( * ) Notice: Subject to any disclaimer, the term of this patent is extended or adjusted under 35 U.S.C. 154(b) by 106 days.

(21) Appl. No.: 12/754,220

(22) Filed: Apr. 5, 2010

(65) Prior Publication Data

US 2010/0187443 A1 Jul. 29, 2010

Related U.S. Application Data

(63) Continuation of application No. 12/186,892, filed on Aug. 6, 2008, now Pat. No. 7,692,172.

(51) Int. Cl.
*A61L 2/10* (2006.01)

(52) U.S. Cl. ............ 250/455.11; 250/504 R; 250/461.1; 250/365; 250/372; 422/1; 422/24; 422/108; 422/186.3; 422/300

(58) Field of Classification Search .................. 250/365, 250/372, 455.11, 453.11, 454.11, 461.1, 250/504 R, 505.1, 507.1, 526; 422/1, 3, 422/22, 24, 107, 108, 119, 186, 186.3, 300
See application file for complete search history.

(56) References Cited

U.S. PATENT DOCUMENTS

| | | | |
|---|---|---|---|
| 3,650,038 A | 3/1972 | Alessi et al. | |
| 5,366,896 A | 11/1994 | Margrey et al. | |
| 5,387,768 A | 2/1995 | Izard et al. | |
| 6,656,424 B1 | 12/2003 | Deal | |
| 6,911,177 B2 | 6/2005 | Deal | |
| 7,034,677 B2* | 4/2006 | Steinthal et al. | 340/539.12 |
| 7,595,023 B2* | 9/2009 | Lewis et al. | 422/62 |
| 7,692,172 B2* | 4/2010 | Leben | 250/504 R |
| 7,931,859 B2* | 4/2011 | Mlodzinski et al. | 422/24 |
| 2006/0070823 A1 | 4/2006 | Huang et al. | |
| 2007/0258852 A1 | 11/2007 | Hootsmans et al. | |

(Continued)

FOREIGN PATENT DOCUMENTS

| | | |
|---|---|---|
| JP | 2003-002565 A | 1/2003 |
| KR | 10-0668938 B1 | 1/2007 |
| WO | WO 2006/041431 A2 | 4/2006 |

*Primary Examiner* — Bernard E Souw
(74) *Attorney, Agent, or Firm* — Hovey Williams LLP (57) ABSTRACT

A system for sanitizing an enclosed structure comprises a first sensor, a second sensor, a third sensor, a germicidal ultraviolet light source, a motor, and a controller. The first sensor detects the presence of humans or animals within the enclosed structure. The second sensor detects the position of at least one door of the enclosed structure. The third sensor detects tampering with the system. The ultraviolet light source provides electromagnetic radiation in the ultraviolet range. The motor moves the ultraviolet light source from an inactive position to an active position and from the active position to the inactive position. The controller receives inputs from the first sensor, the second sensor, and the third sensor, and transmits outputs to the ultraviolet light source and the motor. When the controller receives signals that no humans or animals are present in the enclosed structure and that the door is in a closed position, the controller transmits a signal to the motor to move the ultraviolet light source from the inactive position to the active position and a signal to activate the ultraviolet light source. If humans or animals are detected to be present in the enclosed structure or if the door is detected to be open, then the controller deactivates the ultraviolet light source and repositions the ultraviolet light source.

14 Claims, 9 Drawing Sheets

U.S. PATENT DOCUMENTS

| | | |
|---|---|---|
| 2008/0047329 A1 | 2/2008 | Breed |
| 2008/0282817 A1 | 11/2008 | Breed |
| 2009/0143923 A1 | 6/2009 | Breed |
| 2010/0032589 A1 * | 2/2010 | Leben ..................... 250/504 R |
| 2011/0124035 A1 * | 5/2011 | Broadley et al. ............... 435/29 |
| 2011/0172810 A1 * | 7/2011 | Mlodzinski et al. .......... 700/230 |

* cited by examiner

SYSTEM AND METHOD FOR GERMICIDAL SANITIZING OF AN ELEVATOR OR OTHER ENCLOSED STRUCTURE

RELATED APPLICATION

The present application claims priority benefit, with regard to all common subject matter, of earlier-filed U.S. patent application Ser. No. 12/186,892, filed Aug. 6, 2008, now U.S. Pat. No. 7,692,172 issued Apr. 6, 2010, and entitled "SYSTEM AND METHOD FOR GERMICIDAL SANITIZING OF AN ELEVATOR OR OTHER ENCLOSED STRUCTURE." The identified earlier-filed '172 patent is hereby incorporated by reference in its entirety into the present application.

BACKGROUND OF THE INVENTION

1. Field of the Invention

The present invention relates to systems and methods for sanitizing elevators or other enclosed structures. More particularly, the invention relates to a system and method for germicidal sanitizing of an elevator or other enclosed structure using UV light.

2. Description of the Related Art

Environments where humans and animals gather on a frequent basis, such as schools, medical facilities, and government buildings, may become breeding grounds for a variety of harmful microorganisms, such as bacteria, viruses, fungi, and mold. These harmful microorganisms can result in sickness, infections, disease, and even death. These microorganisms generally grow on surfaces, such as floors and walls, and inside humans and animals, but may also become airborne to cause infection, particularly in a confined space such as an elevator.

Traditional approaches to disinfecting an enclosed structure, such as an elevator, have included the use of liquids and gases. Disinfecting liquids usually include bleach or stronger chemicals, which may have a detrimental, or, at the very least, discoloring effect on the surfaces or materials to which the liquids are applied. In addition, liquids may not be safely applied to electronics or other devices that receive electrical power. Furthermore, liquids may not be applied to substances or materials that are absorbent or are fragile in nature, such as paper. It is also possible that topical liquid antiseptics may induce antibiotic resistance to the very microorganisms they are trying to eradicate. Disinfecting or fumigating gases may include harsh chemicals, such as formaldehyde, which are toxic to humans and animals. Therefore, higher life forms have to be safely removed from the areas where fumigating gases are being used. Additionally, a great amount of time is required for the toxic gas to dissipate from the area once the fumigating is complete. This amount of time may be many hours or even days. Therefore, neither of these approaches is desirable as they introduce toxic agents, require a lot of time, and, of greatest concern, may lead to antibiotic resistance.

SUMMARY OF THE INVENTION

Embodiments of the present invention solve the above-mentioned problems and provide a distinct advance in the art of sanitizing elevators or other enclosed structures. More particularly, embodiments of the invention provide a system and method for germicidal sanitizing of an elevator or other enclosed structure using UV light while preventing unintentional exposure to humans or animals.

Embodiments of the sanitizing system of the present invention comprise a first sensor, a second sensor, a third sensor, an ultraviolet light source, a motor, and a controller. The first sensor is operable to detect the absence of humans within the enclosed structure and to transmit a first input signal when humans are absent. The second sensor is operable to detect the position of at least one door of the enclosed structure and to transmit a second input signal when the door is closed. The third sensor is operable to detect tampering with the system. The ultraviolet light source is operable to provide electromagnetic radiation in the ultraviolet range and to receive a first output signal to activate positioning of the ultraviolet light source. The motor is operable to move the ultraviolet light source and to receive a second output signal to move the ultraviolet light source from an inactive position to an active position. The controller is operable to receive the first input signal and the second input signal, and to transmit the first output signal and the second output signal, wherein the controller transmits the first output signal and the second output signal when the controller receives the first input signal and the second input signal.

Embodiments of the method of steps for sanitizing an enclosed structure performed by the sanitizing system comprise detecting the position of at least one door in the enclosed structure and detecting the absence of humans in the enclosed structure. The method also includes positioning an ultraviolet radiation source within the enclosed structure and activating the ultraviolet radiation source for a predetermined period of time when the door is detected to be in a closed position and humans are detected to be absent. The method further includes deactivating the ultraviolet light source when the door is detected to be in an open position, deactivating the ultraviolet light source when humans are detected to be present, and deactivating the ultraviolet light source when the predetermined period of time has elapsed. The system can also be deactivated if it has been tampered with, such as a person tampering with the UV light source.

This summary is provided to introduce a selection of concepts in a simplified form that are further described below in the detailed description. This summary is not intended to identify key features or essential features of the claimed subject matter, nor is it intended to be used to limit the scope of the claimed subject matter.

Other aspects and advantages of the present invention will be apparent from the following detailed description of the embodiments and the accompanying drawing figures.

BRIEF DESCRIPTION OF THE DRAWING FIGURES

Embodiments of the present invention is described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Figure 1:
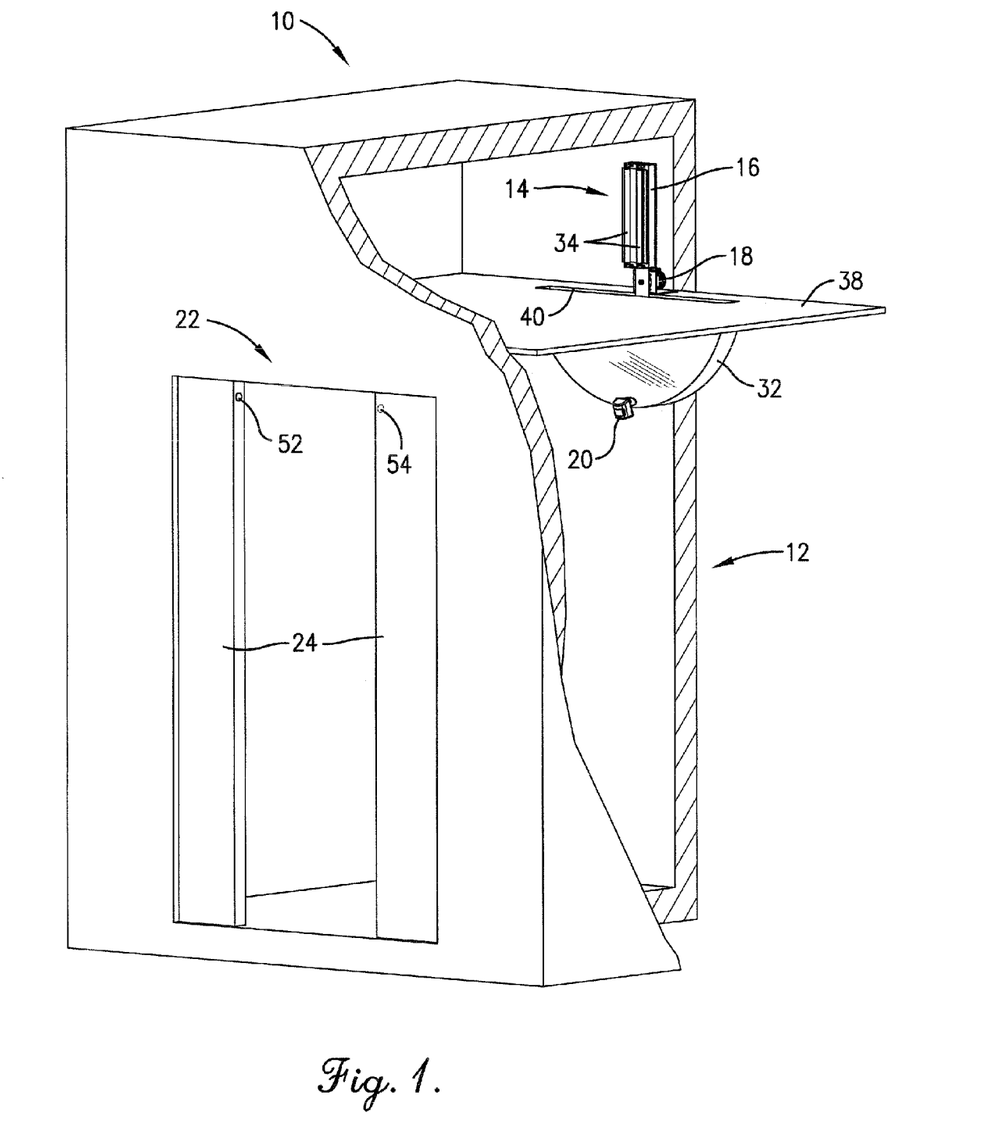
FIG. 1 is a perspective view of a sanitizing system constructed in accordance with various embodiments of the current invention, depicting the cutaway of an elevator.
Figure 2:
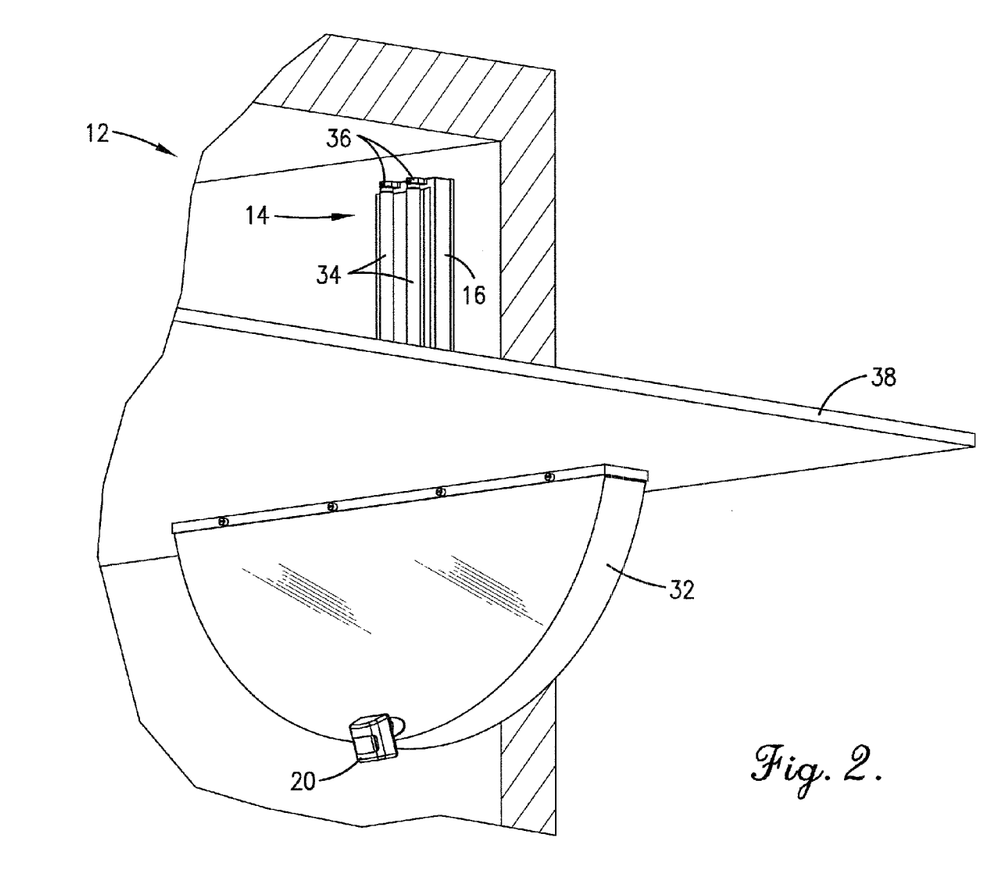
FIG. 2 is an enlarged perspective view of a portion of the sanitizing system.

Turning now to the drawing figures, and particularly FIG. 1, a sanitizing system 10 constructed in accordance with embodiments of the invention is illustrated. The sanitizing system 10 is operable to sanitize or otherwise clean an elevator 12 or other enclosed structure. Although the sanitizing system 10 of the present invention can be used in any enclosed structure where bacteria, viruses, mold, germs, fungi, and other similar microorganisms reside, the detailed description provided below will be with respect to an elevator 12. The sanitizing system 10 of embodiments of the present invention comprises a germicidal ultraviolet ("UV") light source 14 (hereinafter "UV light source"), a first mounting platform 16 on which is mounted the UV light source 14, a motor 18 for rotating or positioning the UV light source 14 in an active position, a first sensor 20 for sensing the presence of a human or animal within the elevator 12, a second sensor 22 for sensing the position of the elevator's doors 24, a third sensor 25 for sensing tampering of the system 10, and a controller 26 for controlling operation of the UV light source 14, including the on/off status (if implemented) and the position of the UV light source 14. The system 10 may also comprise a visible light source 28, a second mounting platform 30 on which the visible light source 28 is mounted, and a protective cover 32.

The UV light source 14 generally serves to provide a source of disinfecting radiation in the ultraviolet electromagnetic ("EM") radiation range. The UV range is generally considered to be EM radiation of a wavelength between approximately 100 nanometers ("nm") and approximately 400 nm. Peak effectiveness for UV radiation as a germicide or disinfectant is between wavelengths of approximately 240 nm and approximately 280 nm. UV radiation between these wavelengths may destroy DNA in living microorganisms and break down organic material found in the air in an indoor environment. The wavelength of the UV light source 14 is generally fixed when the source is manufactured, although in some embodiments, the wavelength of the UV light source 14 may be varied after installation, or during operation.

Figure 3:
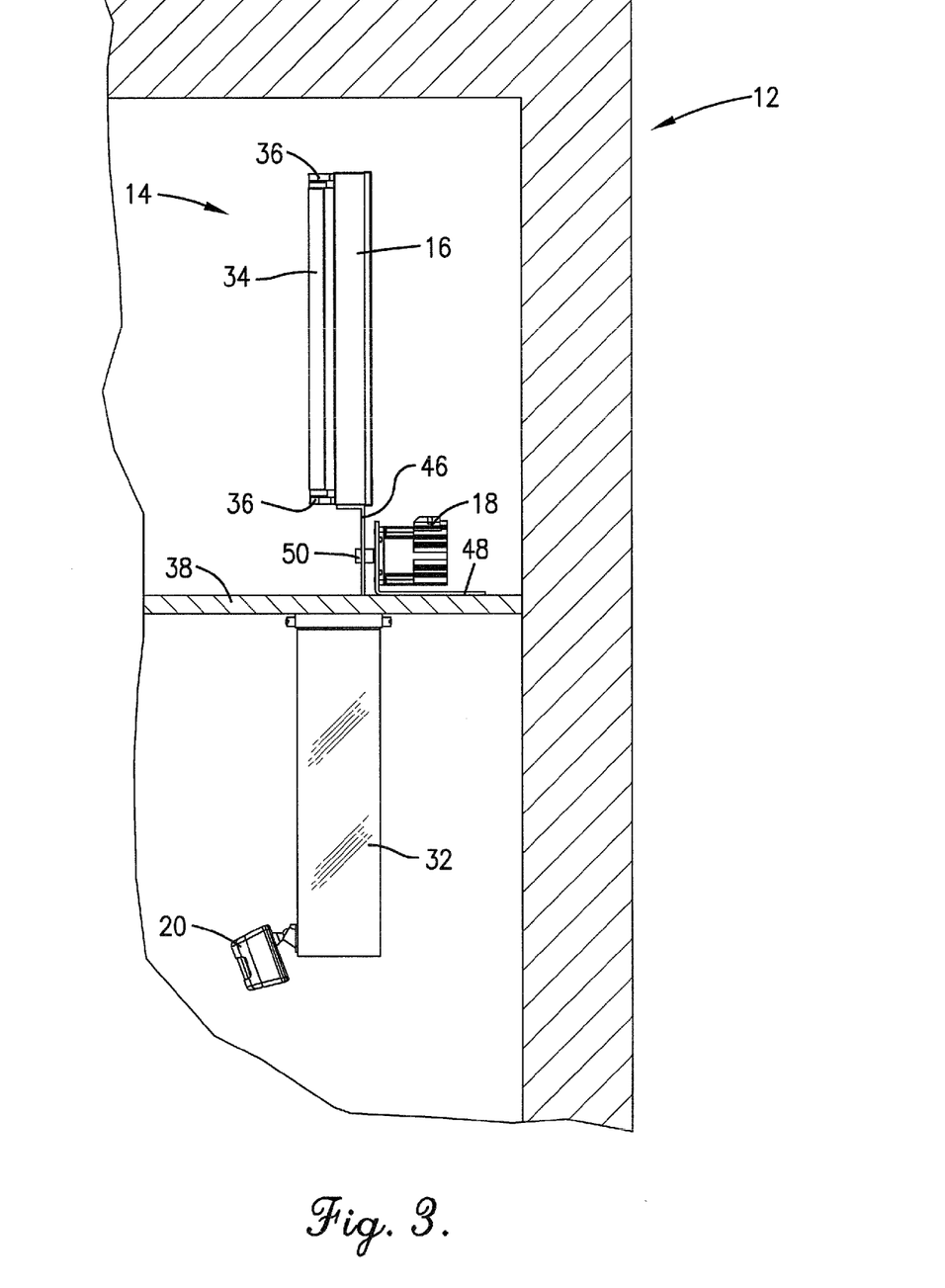
FIG. 3 is a side plan view of a portion of the sanitizing system.
Figure 4:
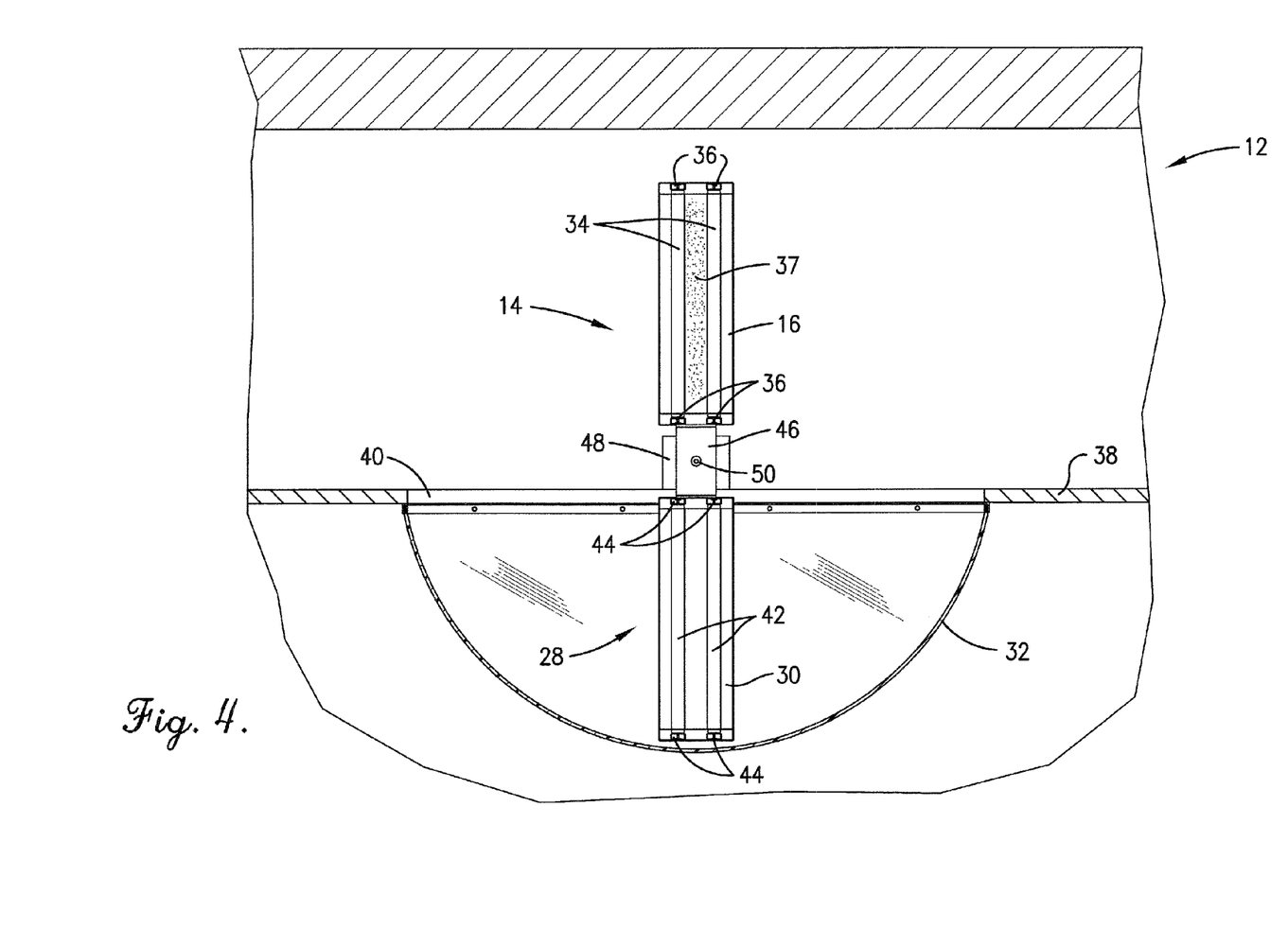
FIG. 4 is a front plan view of a portion of the sanitizing system with a sectional view of a protective cover.

The UV light source 14 may include one or more components operable to emit EM radiation in the UV range, such as lasers, electric arc lamps, pressurized mercury bulbs, or the like. Typically, the UV light source 14 includes one or more tube-shaped bulbs 34 with electrically conductive pins at either one or both ends, such that the UV light source 14 may be plugged into a first electrical socket 36. An electrical voltage is applied to the pins such that the UV light source 14 may be switched on and off like a conventional lamp. The UV light source 14 may also include electrical or electronic components that adjust and maintain the voltage or other electrical properties for the UV light source 14. Operation of the UV light source 14 may be controlled by the controller 26, such that the controller 26 sends a single-bit or a simple encoded signal to the UV light source 14. The UV light source 14 may also send a signal to the controller 26 regarding its status, for example, whether the UV light source 14 is on or off. In preferred operation, the UV light source 14 is powered on at all times, as this reduces the wear on the light source 14 and increases the lifespan of the light source 14. Additionally, when the UV light source is positioned in an inactive position, as described in more detail below, the light source 14 acts as a sanitizer to aerosol in the air. However, if the UV light source 14 is powered on/off, the controller 26 is operable to control powering on/off of the UV light source 14. Typically, the controller 26 communicates with the UV light source 14 through one or more wires and/or electrically conductive cables, although wireless or other communication methods are possible.

The sanitizing system 10 of embodiments of the present invention is operable to be mounted in an elevator 12 or other enclosed structure. As illustrated in FIG. 1, the elevator 12 can be originally manufactured or retrofitted with a drop ceiling 38 that allows room for the UV light source 14 to be positioned in an unexposed area when not in use. An "unexposed area," as used herein, is an area of the elevator 12 or other enclosed structure that is physically separated from an area of the elevator 12 in which humans will be located, such that a majority of the UV light emitted from the UV light source 14 will not be received by any human in the elevator 12. Therefore, the "exposed area," as used herein, is the area of the elevator 12 where humans will reside during their use of the elevator 12. The drop ceiling 38 may also include an opening of sufficient size through which the UV light source 14 may be rotated.

It is advantageous to have the exposed and the unexposed areas in the elevator 12, because UV light can be harmful to a human or animal. In particular, UV light can cause eye damage and skin burns after even a short exposure. Thus, mounting of the UV light source 14 such that it can be positioned in the unexposed area when not in use provides a safety precaution against a human being accidentally exposed to the UV light.

The first mounting platform 16 generally retains or holds the UV light source 14. Specifically, first electrical sockets

36, into which the UV light source bulbs 34 are plugged, are attached to the first mounting platform 16, as seen in FIGS. 3 and 4. The first mounting platform 16 may be of a rectangular shape and sufficient size to accommodate one or more of the UV light source bulbs 34, and may be manufactured from metals, plastics, wood, or other suitable materials. In embodiments of the present invention, the first mounting platform 16 includes a reflective surface 37 positioned on the first mounting platform and directly behind the UV light source 14. Any UV light incident to the reflective surface 37 is reflected off of the surface 37 and into the elevator 12, thereby increasing the efficiency of the UV light source 14. Additionally, a fan 39 may be positioned generally proximate to the UV light source 14 when positioned in the active or inactive position so as to provide air circulation so as to cool the UV light source 14 and prevent it from overheating.

The visible light source 28 generally provides EM radiation of wavelengths in the visible spectrum (approximately 400 nm to approximately 700 nm), or as is commonly known, "light." The visible light source 28 may be the sole source of light in the elevator 12 or may operate in combination with other lights in the elevator 12. The visible light source 28 may include any of a variety of visible light generators, such as incandescent bulbs or fluorescent tubes, as are commonly known. Typically, the visible light source 28 includes one or more tube-shaped bulbs 42 similar in structure and mass to the UV light source bulbs 34 to provide a balanced load to the motor 18, as discussed in more detail below. The visible light source bulbs 42 may also include one or more electrically conductive pins that may be plugged into a second electrical socket 44. Likewise with the UV light source 14, an electrical voltage may be applied to the pins to switch the visible light source 28 on and off. The on/off switching of the visible light source 28 may be controlled by the controller 26 or may be controlled by another system for the elevator 12 or the building in which the elevator 12 is located.

The second mounting platform 30 generally retains the visible light source 28. Particularly, the second electrical sockets 44, into which the visible light bulbs 42 are plugged, are attached to the second mounting platform 30, as seen in FIG. 4. The second mounting platform 30 may be of a rectangular shape and sufficient size to accommodate one or more of the visible light source bulbs 42, and may be manufactured from metals, plastics, wood, or other suitable materials.

The first mounting platform 16 and the second mounting platform 30 may be connected to a first bracket 46, which in turn is coupled to an output shaft 50 of the motor 18. The first bracket 46 may be generally U-shaped and include a first leg, a second leg, and a last portion. The first mounting platform 16 is connected to the first leg of the first bracket 46, and the second mounting platform 30 connected to the second leg of the first bracket 46, as shown in FIG. 4, such that the first mounting platform 16 and the second mounting platform 30 are positioned approximately 180° from each other. A base portion of the first bracket 46 is coupled with the output shaft 50 of the motor 18. Thus, as the output shaft 50 of the motor 18 rotates, the first bracket 46 and, in turn, the first mounting platform 16 with the UV light source 14 and the second mounting platform 30 with the visible light source 28 rotate as well. In addition, it is generally beneficial if the mass of the first mounting platform 16 and the UV light source 14 is roughly equivalent to the mass of the second mounting platform 30 and the visible light source 28 in order to provide a balanced load on the shaft of the motor 18 and provide smooth rotation of the two light sources 14, 28.

The motor 18 may be coupled to a second bracket 48 having an upright leg and a horizontal leg. The second bracket, which mounts the motor 18 to the drop ceiling 38 of the elevator 12, as seen in FIG. 3, near the opening in the drop ceiling 38. The second bracket 48 may also mount the motor 18 to another sturdy fixture of the elevator 12, such as a wall or the top ceiling of the elevator 12. The second bracket 48 may be generally L-shaped, such that the body of the motor 18 is coupled to the upright leg of the second bracket 48. The horizontal leg of the second bracket 48 may be attached to the upper surface of the drop ceiling 38, such that the first bracket 46, the first mounting platform 16, and the second mounting platform 30 are positioned so that they can rotate through the opening in the drop ceiling 38.

The motor 18 generally rotates the UV light source 14 from an inactive position to an active position through the opening in the drop ceiling 38, as seen in FIG. 4. The inactive position of the UV light source 14 is between the drop ceiling 38 and the top ceiling of the elevator 12, also known as the unexposed area. The active position of the UV light source 14 is below the drop ceiling 38, also known as the exposed area, or the main chamber in which people stand while using the elevator 12. Typically, the inactive position is considered to be approximately 90° above the plane of the drop ceiling 38, and the active position is considered to be approximately 90° below the plane of the drop ceiling 38. The output shaft 50 of the motor 18 may be coupled to the base of the first bracket 46, which in turn is attached to the first mounting platform 16 that holds the UV light source 14. Therefore, rotation of the output shaft 50 of the motor 18 approximately 180° in either direction moves the UV light source 14 from the inactive position to the active position. To return from the active position to the inactive position, the output shaft 50 may rotate in the same direction as the first rotation, or may rotate in the opposite direction to return the inactive position. As a result, the motor 18 may be capable of rotating one or more full revolutions in the same direction or roughly half revolutions in opposing directions.

The output shaft 50 of the motor 18 may be manufactured from steel or other hardened metals. The motor 18 may include one or more commonly known electric motors, such as direct current ("DC") motors, alternating current ("AC") motors, brushless motors, universal motors, stepper motors, servo motors, and the like.

The operation of the motor 18 is generally controlled by the controller 26. In various embodiments, the controller 26 may send a single-bit or a simple encoded signal to the motor 18 to adjust the position of the UV light source 14. Accordingly, the motor 18 may also include electrical or electronic components that translate the controller 26 signal into the appropriate electrical signal for the motor 18 to rotate and adjust the position of the UV light source 14. Typically, the controller 26 communicates with the motor 18 through one or more wires and/or electrically conductive cables, although wireless or other communication methods are possible.

The protective cover 32 generally prevents tampering or interfering with the UV light source 14, the visible light source 28, and the motor 18, or any of the other components of the system 10. The protective cover 32 may be of any shape that can cover the opening in the drop ceiling 38, while allowing the first mounting platform 16 and the second mounting platform 30 to rotate freely within the cover. Accordingly, a semi-circular shape may be appropriate with a radius of a circular portion that is at least equal to the length of the longer of either the first mounting platform 16 or the second mounting platform 30, as shown in FIG. 4. The protective cover 32 generally attaches to the lower surface of the drop ceiling 38 around the opening. The protective cover 32 may be manufactured from a hardened material, such as certain types of plastic, metal screen, or quartz, that is transparent or highly transmissive to UV light in order to allow UV exposure of the interior of the elevator 12.

The first sensor 20 generally detects the presence of humans or animals in the elevator 12. The first sensor 20 is usually positioned within the elevator 12 in a location that allows access to the entire volume, or at least a majority of the volume, of the interior of the elevator 12. One location may be at the bottom of the protective cover 32, such that the first sensor 20 faces the doors 24 of the elevator 12, as shown in FIG. 1. The first sensor 20 may be operable to detect any one of or combinations of a variety of parameters, such as motion, heat, sound, reflected or transmitted light, or the like. The first sensor 20 may include one or more of the following: motion or movement detectors or sensors, thermal or infrared detectors, sensors, or imagers, microphones, sonic or ultrasonic transducers, lasers, light-emitting diodes (LEDs), photodetectors, photoresistors, and the like.

The first sensor 20 generally transmits a single-bit or simple encoded signal to the controller 26 to indicate the presence or absence of human beings or animals inside the elevator 12 and may include additional electronics to generate that signal. The first sensor 20 may communicate with the controller 26 electrically through one or more wires or electrically conductive cables, or wirelessly utilizing one or more radio frequency ("RF") transmitters and receivers.

The second sensor 22 generally detects the position of the doors 24 of the elevator 12. More specifically, the second sensor 22 detects when the doors 24 are closed. Thus, the second sensor 22 may be positioned very close to the elevator doors 24. Typically, the second sensor 22 is located on the portion of the doors 24 that touches when the doors 24 close. The second sensor 22 usually includes a first subsensor 52 and a second subsensor 54 that work in combination to determine whether the elevator doors 24 are closed. In such an embodiment, the second sensor 22 generates a "door closed" signal when the first subsensor 52 is in close proximity to, or physically touching, the second subsensor 54. Therefore, the first subsensor 52 is located on the mating portion of one elevator door while the second subsensor 54 is located on the mating portion of the other elevator door in alignment with the first subsensor 52, such that when the elevator doors 24 close, the first subsensor 52 contacts the second subsensor 54, as seen in FIG. 1. As can be appreciated, if the design of the elevators doors 24 is different, for example, if one door slides or telescope within another door, then the second sensor 22, including the first and second subsensors 52,54, may be placed in a location different from the location described above.

The first and second subsensors 52, 54 may include simple electrical contacts that generate a signal or complete an electric circuit when they touch. The first and second subsensors 52, 54 may also include pressure or limit switches that activate under mechanical contact, magnetic elements, optical elements, or any combination thereof. The second sensor 22 may also include additional electrical or electronic components that adapt or adjust the signal from the first subsensor 52 and the second subsensor 54 that are transmitted to the controller 26. The second sensor 22 may communicate with the controller 26 electrically through one or more wires or electrically conductive cables, or wirelessly utilizing one or more RF transmitters and receivers.

The third sensor 25 generally detects any tampering with the system 10 of embodiments of the present invention, including without limitation tampering with the UV light source 14, the motor 18, the controller 26, and/or the visible light source 28. The third sensor 20 may be positioned proximate to the UV light source 14, although multiple subsensors (not shown) may be positioned at any one of or combination of the above UV light source 14, motor 18, controller 26, and visible light source 28. The third sensor 25 may include one or more of the following: motion or movement detectors or sensors, thermal or infrared detectors, sensors, or imagers, microphones, sonic or ultrasonic transducers, lasers, light-emitting diodes (LEDs), photodetectors, photoresistors, and the like.

The third sensor 25 generally transmits a single-bit or simple encoded signal to the controller 26 to indicate movement beyond a pre-defined tolerance or other tampering of the UV light source 14, motor 18, controller 26, and visible light source 28 and may include additional electronics to generate that signal. The third sensor 25 may communicate with the controller 26 electrically through one or more wires or electrically conductive cables, or wirelessly utilizing one or more radio frequency ("RF") transmitters and receivers.

Figure 11:
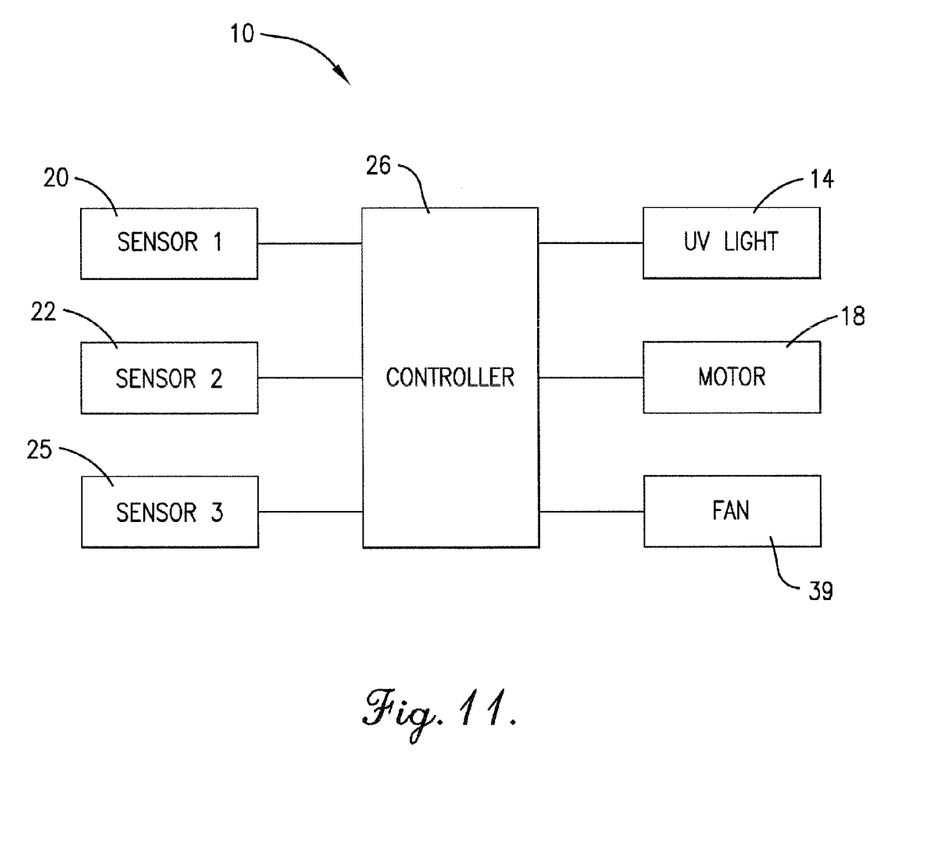
FIG. 11 is a block diagram of the sanitizing system.

The controller 26 generally receives input data from the first sensor 20, the second sensor 22, and the third sensor 25 and transmits control signals to the motor 18 and the UV light source 14, as shown in FIG. 11. The conditions that the first sensor 20 and the second sensor 22 monitor lend themselves very well to binary representation. For example, the first sensor 20 detects the presence or absence of people in the elevator 12, and the second sensor 22 detects whether the elevator doors 24 are opened or closed. Hence, the signals from the first sensor 20 and the second sensor 22 may be in binary form—a "0" for one condition and a "1" for the other condition. The first sensor 20 and second sensor 22 signals may also be in a simple encoded form to provide error detection and correction capabilities. Likewise, the operation of the motor 18 and positioning of the UV light source 14 may be implemented with binary signals. For example, the motor 18 may receive an on/off signal or may receive a single pulse signal to instruct the motor 18 to move the UV light source 14 a predetermined amount. The UV light source 14 may also receive an on/off signal from the controller 26, if desired. Therefore, the signals from the controller 26 to the motor 18 and the UV light source 14 may be, for example, a "0" for off and a "1" for on. The motor 18 and UV light source 14 signals may also be in a simple encoded form to provide error detection and correction capabilities.

The controller 26 may be implemented in hardware, software, firmware, or combinations thereof. The controller 26 may include a processing element coupled with a memory element that in combination are able to execute software code segments that implement the control function. The controller 26 may also include microcomputers, microprocessors, microcontrollers, programmable intelligent computers (PICs), field-programmable gate arrays (FPGAs), programmable logic devices (PLDs), programmable logic controllers (PLCs), and the like. The controller 26 may also be formed or created from one or more code segments of a hardware description language (HDL). The controller 26 may also include a memory component such as hard-disk drives, optical disks, floppy disks, random-access memory (RAM), read-only memory (ROM), cache memory, programmable ROM (PROM), erasable PROM (EPROM), and the like. In addition, the controller 26 may include other data input devices such as keyboards, keypads, mice or other pointing devices, knobs, buttons, switches, and the like. The controller 26 may include other data output devices such as screens, monitors, displays, speakers, LEDs, liquid crystal displays ("LCDs"), and the like. Furthermore, the controller 26 may include data interfaces, such as a computer network interface, to allow the system 10 to send and receive data from other computers, networks, or systems. Additionally, the controller may be operable with a mainframe controller for the building in which the elevator is housed.

The controller 26 may also include one or more timing elements. The timing elements may include count-down timers that wait for a predetermined amount of time, and count-up timers that measure the duration of an event.

Figure 12:
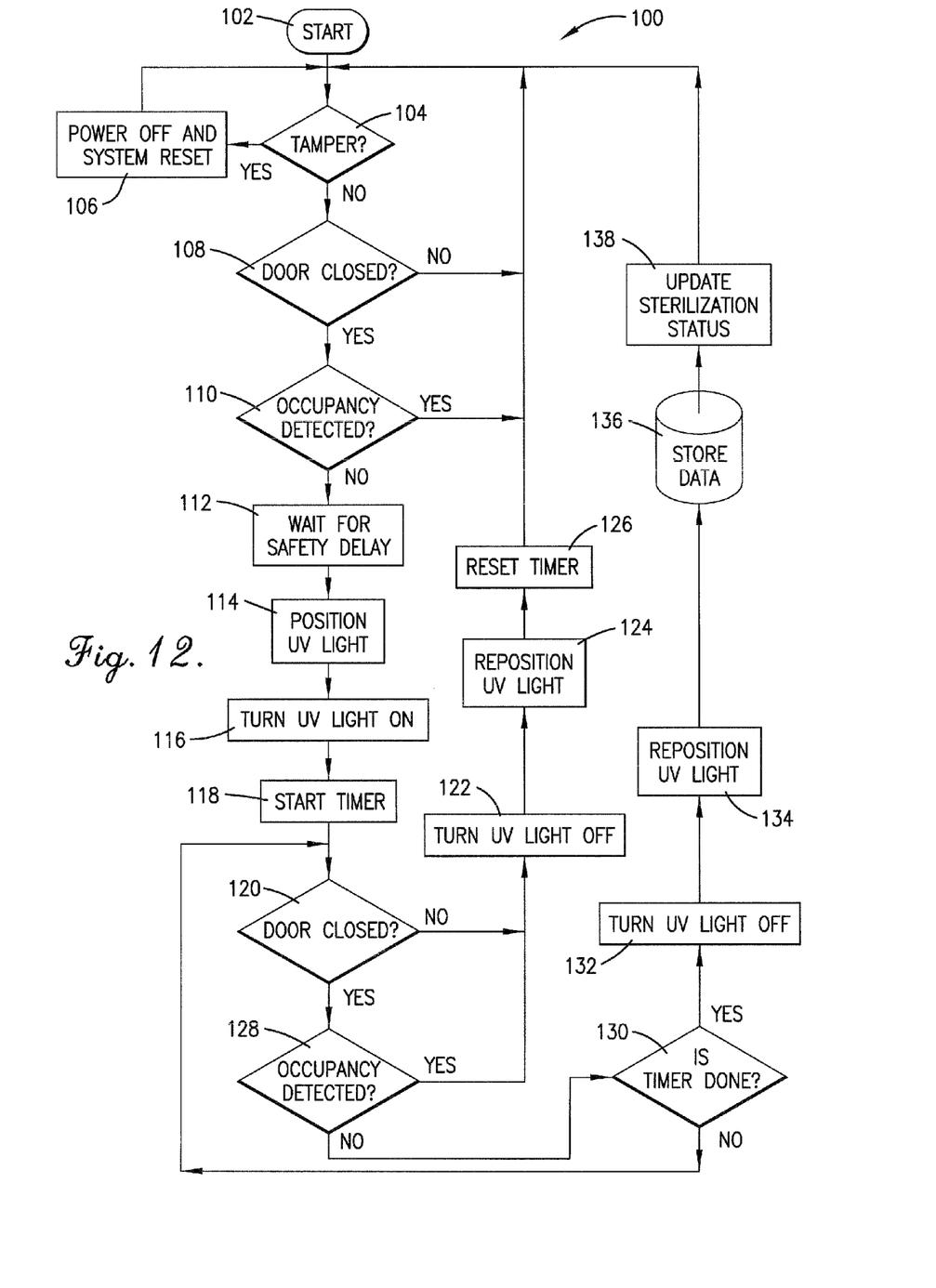
FIG. 12 is a flow diagram of some of the steps that may be performed by the sanitizing system.

The sanitizing system 10 in accordance with various embodiments of the current invention may operate as illustrated in the flow diagram 100 of FIG. 12. The flow diagram 100 as shown in FIG. 12 provides the general flow of operation for the system 10; however, certain steps may be performed concurrently or otherwise out of order from what is shown in FIG. 12. The system 10 operation starts at block 102 in a default state. The controller 26 may checks for tampering at block 104. The controller 26 may check the signals it is receiving from the first sensor 20, the second sensor 22, and the third sensor 25, or the controller 26 may receive feedback from the UV light source 14 or the motor 18. If any of these signals are abnormal, the controller 26 may power off and reset the system 10 as indicated at block 106. Alternatively, the controller 26 may perform a self diagnostic check. If any errors are found, the system 10 may be reset. After a reset, the system 10 may return to the start point at block 102.

The controller 26 checks the input from the second sensor 22 to determine if the elevator doors 24 are closed at block 108. The second sensor 22 may send a simple binary signal to the controller 26 to indicate yes or no. If the doors 24 are open and the answer is no, the system 10 may return to the start point at block 102. If the doors 24 are closed and the answer is yes, the controller 26 checks the input from the first sensor 20 to determine if the elevator 12 is occupied at block 110. The first sensor 20 may send a simple binary signal to the controller 26 to indicate yes or no. If the answer is yes and the elevator 12 is occupied, the system 10 may return to the start point at block 102. If the answer is no and the elevator 12 is unoccupied, the controller 26 may prepare to sterilize the elevator 12.

The controller 26 may wait for a safe amount of time, utilizing one or more timing elements as indicated at block 112. The controller 26 may then position the UV light source 14 at block 114 from the inactive position to the active position. The controller 26 may send an on signal to the motor 18 to rotate the UV light source 14 followed by an off signal when the UV light is in position. Alternatively, the controller 26 may send a pulse signal to the motor 18 to rotate by a predetermined amount—generally approximately 180°. As noted above, in preferred operation, the UV light source 14 is powered on at all times, and therefore, the controller need not instruct the light source 14 to power on/off in response to positioning of the light source 14. However, if the UV light source 14 is powered on/off in response to positioning of the light source at block 114, then the controller 26 may turn the UV light source 14 on at block 116. The controller 26 may send a simple binary signal to the UV light source 14 to turn it on.

Figure 7:
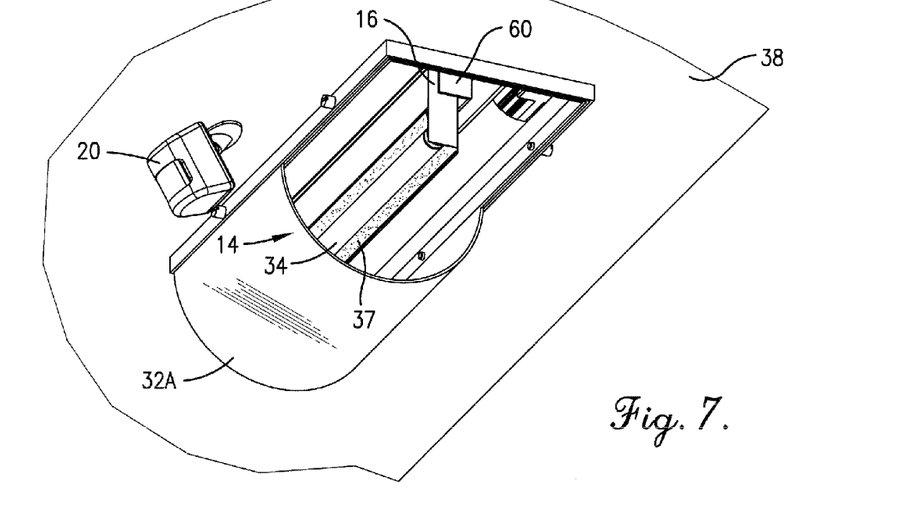
FIG. 7 is a lower perspective view of a portion of the second embodiment of the sanitizing system with a sectional view of the protective cover, depicting the ultraviolet light source in the active position.
Figure 8:
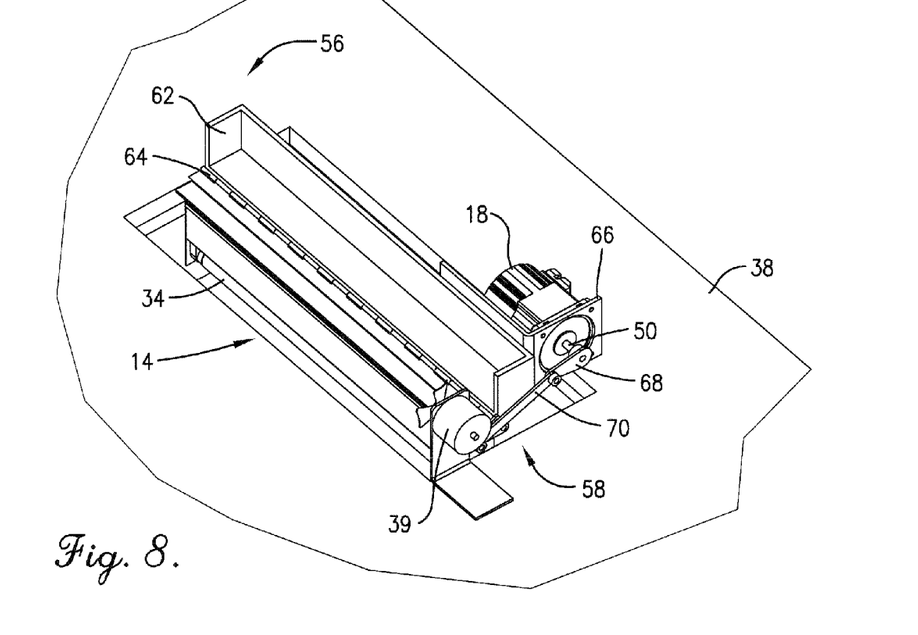
FIG. 8 is an upper perspective view of a portion of the second embodiment of the sanitizing system, depicting the ultraviolet light source in the active position.

Once the light is positioned in the active position, as illustrated in FIGS. 7 and 8, the controller 26 may start the timing element at block 118 to implement a proper sanitizing cycle. The duration that the UV light source 14 is on, and thus, the duration of the sanitizing cycle, depends on a number of factors including, but not limited to, the size of the elevator 12 (particularly the longest dimension of the elevator 12), the intensity of the UV output from the UV light source 14, and the type of microorganism that is targeted. Various microorganisms require different incident energies, and in turn different exposure times, to be disabled or have their growth inhibited.

For safety purposes, while the UV light source 14 is in the active position, the first sensor 20 and the second sensor 22 still need to be monitored to prevent accidental exposure to humans or other animals. The controller 26 checks the input from the second sensor 22 to see if the elevator doors 24 are closed at block 120. If the answer is no and the doors 24 are starting to open, the controller 26 turns the UV light source 14 off at block 122. This option of powering off the UV light source 14 is preferred due to the possibility of unsafe exposure to a human. The controller 26 may send a binary off signal to the UV light source 14. The controller 26 repositions the UV light source 14 at block 124 from the active position to the inactive position. As described above, the controller 26 may send an on signal to the motor 18 to rotate the UV light source 14 followed by an off signal when the UV light is in position, or the controller 26 may send a pulse signal to the motor 18 to rotate approximately 180°. The controller 26 resets the timing elements at block 126, and the system 10 may return to the start point at block 102.

If elevator doors 24 are still closed, the controller 26 checks the input from the first sensor 20 to see if the elevator 12 is occupied at block 128. While it is not likely that the elevator 12 is occupied at this point, it may be possible. If the signal from the first sensor 20 is yes and the elevator 12 is occupied, then the controller 26 turns the UV light source 14 off at block 122. The system 10 may then follow the steps discussed above for blocks 124 and 126.

If the elevator doors 24 are closed and the elevator 12 is unoccupied, the controller 26 checks the timer to see if the sanitizing cycle is complete. If the timing element has not finished, then the controller 26 performs a safety check to see if the doors 24 are closed and the elevator 12 is unoccupied as discussed above at blocks 120 and 128. If the timing element has finished and the sanitizing cycle is complete, the controller 26 repositions the UV light source 14 to the inactive position at block 134. Alternatively, if the UV light source 14 is being powered on/off dependent on positioning, then the UV light source 14 may be first powered off at block 132. At this point, the controller may instruct the fan 39 to power on so as to provide air circulation proximate to the UV light source 14 so as to cool the UV light source 14. The controller 26 stores any relevant data concerning the sanitizing cycle at block 136. The controller 26 may update the sterilization status at block 138 and return to the start point at block 102.

Again and as noted above, when the UV light source 14 is positioned above the drop ceiling in the inactive position and in the unexposed area, the UV light source 14 is preferably still turned on, such that it is exposing the air to the UV light, also referred to as aerosol. This provides a system and method of sanitizing the air when the UV light source 14 is not in active use in the exposed area of the elevator 12.

A second embodiment for the sanitizing system 10 is shown in FIGS. 5-10. The system 10 may comprise the UV light source 14, the first mounting platform 16, the motor 18, the first sensor 20, the second sensor 22, the third sensor 25, and the controller 26, all as described above. The system 10 may further comprise a rotatable shelf 56 to which the first mounting platform 16 is attached, and a linking mechanism 58 that couples the shelf 56 to the motor 18. In addition, the system 10 may include a protective cover 32A similar to the one described above.

Figure 6:
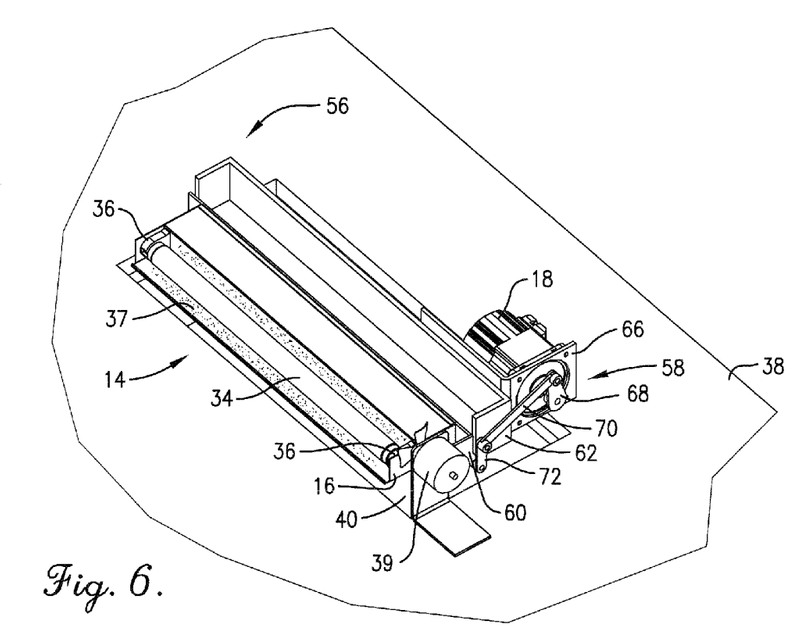
FIG. 6 is an upper perspective view of a portion of the second embodiment of the sanitizing system, depicting the ultraviolet light source in the inactive position.

The shelf 56 may include a front portion 60 and a rear portion 62 with a hinge 64 coupling the front portion 60 to the rear portion 62, and allowing the front portion 60 to rotate about the rear portion 62 while the rear portion 62 remains stationary, as seen best in FIGS. 6 and 8. The front portion 60 of the shelf 56 may be elongated so it can receive the first mounting platform 16. In embodiments of the present invention and as illustrated in FIG. 7, the rear portion 62 of the shelf 56 may include the reflective surface 37. The surface 37 is preferably positioned directly behind the UV light source 14. Any UV light incident to the reflective surface 37 is reflected off of the surface 37 and into the elevator 12, thereby increasing the efficiency of the UV light source 14. Additionally, and as with the first embodiment, the fan 39 may be positioned proximate to the UV light source 14 when it is positioned in the active and inactive position.

In certain embodiments, the front portion 60 of the shelf 56 may be integrated with or may be the same component as the first mounting platform 16. The front portion 60 of the shelf 56 may be connected to the linking mechanism 58. The rear portion 62 of the shelf 56 may be connected to a third bracket 66.

Figure 10:
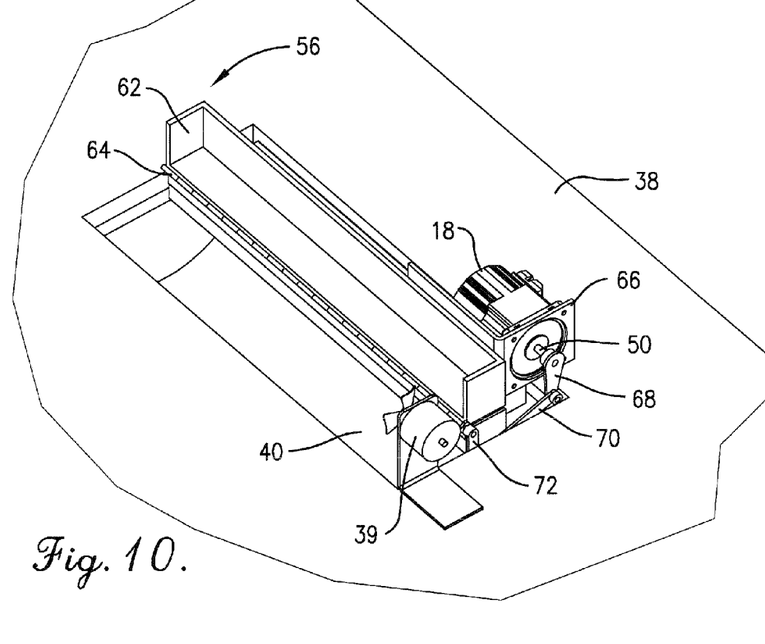
FIG. 10 is an upper perspective view of a portion of embodiments of the sanitizing system, depicting the ultraviolet light source rotated approximately 180° from the inactive position.

The third bracket 66 generally couples the shelf 56 to the motor 18, and may be L-shaped with the shelf 56 connected to the outer surface of one leg and the motor 18 connected through an opening on the inner surface of the other leg, as shown in FIGS. 6, 8, and 10. The motor 18 may be coupled to the upper surface of the drop ceiling 38 at the edge of the opening in the drop ceiling 38. Thus, the shelf 56 with the first mounting platform 16 and the UV light source 14 attached may be positioned directly over the opening in the drop ceiling 38.

The linking mechanism 58 couples the front portion 60 of the shelf 56 to the output shaft 50 of the motor 18. The linking mechanism 58 may include first, second, and third linking components 68, 70, 72 of varying lengths that are coupled together end to end. The first linking component 68 is coupled to the output shaft 50 of the motor 18 and the third linking component 72 is coupled to the front portion 60 of the shelf 56, such that rotation of the output shaft 50 of the motor 18 results in rotation of the front portion 60 of the shelf 56.

Figure 5:
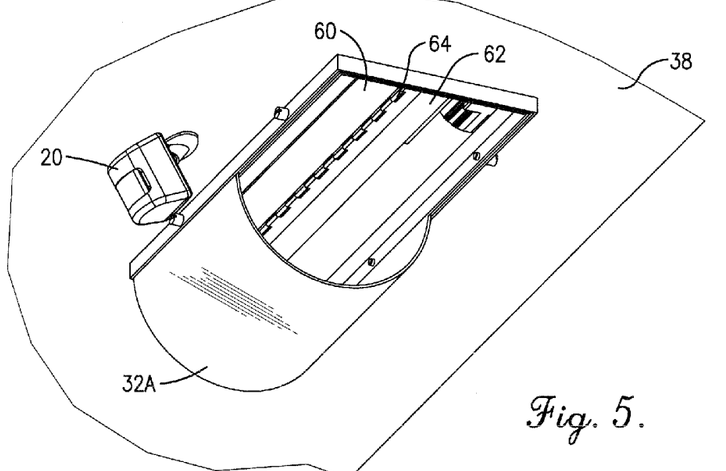
FIG. 5 is a lower perspective view of a portion of a second embodiment of the sanitizing system with a sectional view of the protective cover, depicting an ultraviolet light source in an inactive position.
Figure 9:
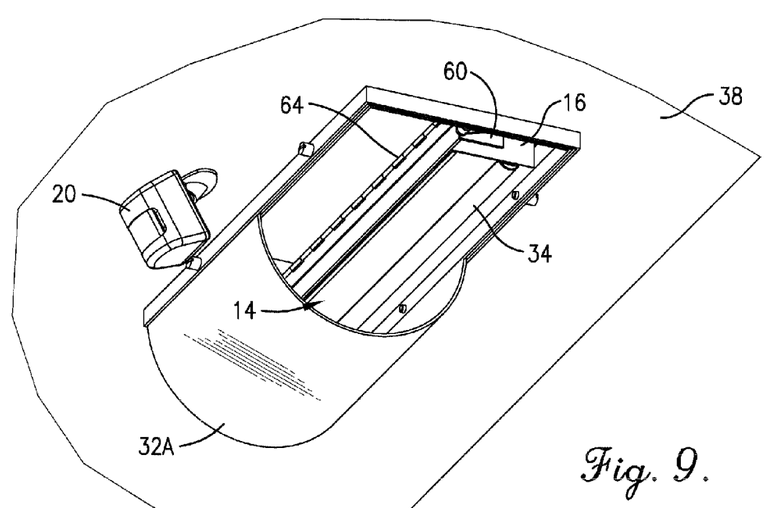
FIG. 9 is a lower perspective view of a portion of embodiments of the sanitizing system, depicting a sectional view of the protective cover and the ultraviolet light source rotated approximately 180° from the inactive position.

The motor 18 generally rotates the UV light source 14 from an inactive position to an active position through the opening in the drop ceiling 38, as seen in FIGS. 5-10. In the second embodiment, the inactive position is where the first mounting platform 16 is approximately parallel to the plane of the drop ceiling 38 with the UV light source 14 facing generally upward, as illustrated in FIGS. 5 and 6. The active position is where the first mounting platform 16 is approximately perpendicular to the plane of the drop ceiling 38 with the UV light source 14 facing generally outwards, as illustrated in FIGS. 7 and 8. In most elevators 12, the system 10 will be positioned within the ceiling of the elevator 12 proximate to a general middle of a back wall of the elevator 12. This location allows for the largest exposure area of the UV light. However, in some instances, it may be desired to place multiple sanitizing systems 10 within the elevator 12 or other enclosed structure, especially if a location of only one system 10 will not allow UV light to be exposed to a majority of the surfaces having microorganisms thereon. In this or other instances, it may be desired for the UV light source to rotate 180° from the inactive position, as illustrated in FIGS. 9 and 10. As can be appreciated, the UV light source 14 may be rotated to any desired angle depending on the desired exposure area.

The motor 18 of the second embodiment may rotate the output shaft 50 in one direction to move the UV light source 14 from the inactive position to the active position. However, the motor 18 is generally required to rotate the output shaft 50 in the opposite direction to return the UV light source 14 from the active position to the inactive position. For example, if the output shaft 50 rotated in the clockwise direction to move the UV light source 14 from the inactive position to the active position, the output shaft 50 would rotate in the counterclockwise direction to move the UV light source 14 from the active position to the inactive position. This requirement is due to the structure of the shelf 56. Since the rear portion 62 of the shelf 56 is stationary, the front portion 60 must rotate in the reverse direction to return the UV light source 14 to the inactive position. Thus, the motor 18 of the second embodiment may include additional electrical or electronic circuitry to rotate in the appropriate direction when it receives a signal from the controller 26 to position the UV light source 14.

The protective cover 32A utilized in the second embodiment, in similar fashion to the embodiments described above, is also attached to the lower surface of the drop ceiling 38 around the perimeter of the opening in the drop ceiling 38, as shown in FIGS. 5, 7, and 9. The protective cover 32A also has a semi-circular shape, as seen in cutaway in FIGS. 5, 7, and 9. However, the cover is elongated to match the length of the axis of rotation for the front portion 60 of the shelf 56, and in turn the first mounting platform 16 and the UV light source 14. Thus, the radius of curvature of the protective cover 32A is large enough to accommodate the motion of the UV light source 14 as it rotates from the inactive position to the active position and back. Likewise, with the protective cover 32 discussed above, the protective cover 32A is generally transparent or highly transmissive to the radiation of the UV light source 14. Although use of the protective cover 32A is described, in some embodiments of the present invention, the protective cover 32A may not be used.

The sanitizing system 10 of the second embodiment operates in a substantially similar fashion as the embodiments described above with regard to the flow diagram of FIG. 12. Although the UV light source 14 of the second embodiment is oriented differently from the UV light source 14 of the embodiments described above, the performance of the system 10 is not substantially affected. The system 10 of the second embodiment follows the steps of FIG. 12 in substantially the same way as discussed above.

The sanitizing system 10 in accordance with various embodiments of the current invention has been disclosed to be utilized with an elevator 12. However, the sanitizing system 10 as disclosed herein may be utilized with any confined space or enclosed structure where humans or animals visit or congregate but that may be evacuated and sealed off to prevent unintentional exposure of UV radiation to the humans or animals during a sanitizing cycle. In such implementations, additional sensors may be used to detect the position of additional doors, windows, or other portals. Examples of confined spaces or enclosed structures include, but are not limited to, hospital rooms, surgical operating rooms, medical examining rooms, veterinary offices and operating rooms, hotel rooms, public restrooms, public libraries, school/class rooms, day care centers, government offices, court rooms, meeting halls, residential houses, churches or religious buildings, and the like.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A sanitizing system for use with an enclosed structure, the system comprising:
   a first sensor to detect the absence of humans within the enclosed structure and to transmit a first input signal when humans are absent;
   a second sensor to detect the position of at least one door of the enclosed structure and to transmit a second input signal when the door is closed;
   a germicidal ultraviolet light source to provide electromagnetic radiation in the ultraviolet range and to receive a first output signal to activate the ultraviolet light source; and
   a controller to receive the first input signal and the second input signal, and to transmit the first output signal,
   wherein the controller transmits the first output signal when the controller receives the first input signal and the second input signal.

2. The system of claim 1, wherein the controller no longer transmits the first output signal when the controller no longer receives the first input signal or the second input signal.

3. The system of claim 1, wherein the first sensor includes a motion detector.

4. The system of claim 1, wherein the first sensor includes a thermal sensor.

5. The system of claim 1, further including a third sensor for detecting tampering with the sanitizing system.

6. A sanitizing system for use with an enclosed structure, the system comprising:
   a first sensor to detect the presence or absence of humans within the enclosed structure and to transmit a first input signal indicating one of a human present or absent in the enclosed structure;
   a second sensor to detect the position of at least one door of the enclosed structure and to transmit a second input signal indicating one of the door being closed or open;
   a germicidal ultraviolet light source to provide electromagnetic radiation in the ultraviolet range and to receive a first output signal to activate the ultraviolet light source; and
   a controller to receive the first input signal and the second input signal, and to transmit the first output signal,
   wherein the controller transmits the first output signal when the controller receives the first input signal indicating the absence of any human in the enclosed structure and the second input signal indicating the door of the enclosed structure being closed.

7. The system of claim 6, further including a mounting platform on which the ultraviolet light source is mounted, the mounting platform further including a reflective surface for reflecting UV light incident to the surface.

8. The system of claim 6, wherein the first sensor includes a motion detector.

9. The system of claim 6, wherein the first sensor includes a thermal sensor.

10. The system of claim 6, further including a motor to move the ultraviolet light source and to receive a second output signal to move the ultraviolet light source from an inactive position to an active position.

11. A method for sanitizing an enclosed structure, the method comprising the steps of:
   a) detecting the position of at least one door providing access for humans to the enclosed structure;
   b) detecting the absence of humans in the enclosed structure;
   c) activating an ultraviolet light source for a predetermined period of time when the door is detected to be in a closed position and humans are detected to be absent from the enclosed structure;
   d) if the door is detected to be in an open position or if at least one human is detected to be present in the exposed area, deactivating the ultraviolet light source; and
   e) deactivating the ultraviolet light source once the predetermined period of time has elapsed.

12. The method of claim 11, wherein the step of detecting the door in the closed position is accomplished using a sensor.

13. The method of claim 11, wherein detecting the absence of humans in the enclosed structure is accomplished using a motion detector.

14. The method of claim 11, wherein detecting the absence of humans in the enclosed structure is accomplished using a thermal sensor.

* * * * *